(12) United States Patent
Leclercq

(10) Patent No.: US 6,770,097 B2
(45) Date of Patent: Aug. 3, 2004

(54) KIT FOR A KNEE JOINT PROSTHESIS

(75) Inventor: Vincent Leclercq, Winterthur (CH)

(73) Assignee: Centerpulse Orthopedics Ltd., Baar (CH)

( * ) Notice: Subject to any disclaimer, the term of this patent is extended or adjusted under 35 U.S.C. 154(b) by 67 days.

(21) Appl. No.: 09/732,036

(22) Filed: Dec. 6, 2000

(65) Prior Publication Data

US 2001/0003803 A1 Jun. 14, 2001

(30) Foreign Application Priority Data

Dec. 13, 1999 (EP) .............................................. 9981151

(51) Int. Cl.⁷ ................................................ A61F 2/38
(52) U.S. Cl. .................................. 623/20.15; 623/20.31
(58) Field of Search ........................... 623/20.14–20.34

(56) References Cited

U.S. PATENT DOCUMENTS

| | | | | |
|---|---|---|---|---|
| 4,298,992 A | * | 11/1981 | Burstein et al. .............. | 3/1.911 |
| 4,892,547 A | * | 1/1990 | Brown ......................... | 623/20 |
| 4,950,297 A | | 8/1990 | Elloy | |
| 5,116,375 A | * | 5/1992 | Hofmann ..................... | 623/20 |
| 6,099,570 A | * | 8/2000 | Livet et al. ............... | 623/20.21 |
| 6,264,696 B1 | * | 7/2001 | Reigner et al. .......... | 623/20.24 |
| 6,264,697 B1 | * | 7/2001 | Walker ..................... | 623/20.27 |

FOREIGN PATENT DOCUMENTS

| | | | | |
|---|---|---|---|---|
| EP | 0553585 A2 | 8/1993 | | |
| EP | 0913132 A1 | 5/1999 | | |
| WO | WO 99/13804 | * | 3/1999 | ............. A61F/2/38 |

* cited by examiner

Primary Examiner—Corrine McDermott
Assistant Examiner—Hieu Phan
(74) Attorney, Agent, or Firm—Townsend and Townsend and Crew LLP

(57) ABSTRACT

A kit for a knee joint prosthesis includes a tibia part, a femur part and a meniscus part which is to be arranged between the femur part and the tibia part. The kit enables the assembly of different prosthesis types, namely of prostheses in which the meniscus part is arranged to be immobile relative to the tibia part and of prostheses in which the meniscus part is arranged so as to be movable relative to the tibia part. The kit includes a plurality of guiding elements which are formed in such a manner that the respective guiding element is in engagement with the tibia part and with the meniscus part when the prosthesis is assembled and determines the movability of the meniscus part relative to the tibia part.

4 Claims, 2 Drawing Sheets

1

KIT FOR A KNEE JOINT PROSTHESIS

BACKGROUND OF THE INVENTION

1. Field of the Invention

The invention relates to a kit for a knee joint prosthesis.

2. Description of the Prior Art

Knee joint prostheses are already obtainable on the market in a wide variety. The tendency is increasingly towards designing the prostheses to be modular in order to allow the surgeon the possibility where appropriate even during the operation of taking the actual anatomical conditions of the patient (e.g. quality of the bone, quality of the ligaments, etc.) into consideration in an ideal manner in the choice of the type of the prosthesis.

In knee joint prostheses which comprise a tibia part in which a meniscus part is provided on the surface facing the femur, a distinction in principle between the following four types should be made with respect to the kind of movability of the meniscus part relative to the surface of the tibia part facing the femur: prostheses with a meniscus part which is arranged to be immobile relative to this surface of the tibia part, prostheses with a meniscus part which is arranged to be exclusively rotatable relative to this surface of the tibia part, prostheses with a meniscus part which is arranged to be exclusively translationally displaceable relative to this surface of the tibia part, and prostheses with a meniscus part which is arranged to be both rotatable and translationally displaceable relative to this surface of the tibia part.

Whereas the individual types of such knee joint prostheses—taken by themselves—are already known, it is at least the case that those meniscus parts which are arranged to be immobile relative to the surface of the tibia part facing the femur are regularly connected firmly and unreleasably to or to be releasable only with great difficulty from the tibia part, e.g. with the help of snap connections, such as are shown in EP-A-0,923,916. A prosthesis in which the meniscus part is arranged to be exclusively translationally displaceable relative to the surface of the tibia part facing the femur is for example known from EP-A-0,913,132. A prosthesis in which the meniscus part is arranged to be both rotatable and translationally displaceable relative to the surface of the tibia part facing the femur is for example known from EP-A-0,519,873.

Disadvantageous is however that different tibia parts are required at least for those prostheses in which the meniscus part is firmly connected to the tibia part, e.g. by means of the snap connections, and for those prostheses in which the meniscus part is movable—in whatsoever way—relative to the tibia part. The tibia part for the immobile meniscus part must in addition have additional means for the securing of the meniscus part (e.g. projections which enter into a snap connection with corresponding projections at the meniscus part), which makes the manufacture of the tibia part and of the meniscus part more complicated and expensive and also often leads to the tibia plateau of the tibia part on which the meniscus part lies becoming thinner. In addition the meniscus part is also formed to be thinner at its periphery, that is, where it comes to lie over the projections (for forming the snap connection) of the tibia part, which on the one hand is more complicated and expensive in the technical manufacture and on the other hand partly exposes the meniscus part to extreme stresses in these regions.

SUMMARY OF THE INVENTION

The object of the invention is therefore to propose a kit for a knee joint prosthesis which does not have the above-named disadvantages, but at the same time however maintains the intra-operative flexibility for the operating surgeon with respect to the type of knee joint prosthesis to be implanted.

The kit in accordance with the invention comprises a plurality of guiding elements which are formed in such a manner that the respective guiding element is in engagement with the tibia part and with the meniscus part when the prosthesis is assembled and determines the movability of the meniscus part relative to the tibia part. It is thus—for a given meniscus part—possible to determine through the choice of a corresponding guiding element whether the meniscus part is arranged immovably relative to the tibia part when the prosthesis is assembled or whether the meniscus part is arranged to be movable relative to the tibia part, and thus can be moved on the tibia plateau. In this the movability on the tibia plateau can mean that the meniscus part is either exclusively rotatable or exclusively translationally displaceable or both rotatable and translationally displaceable.

Moreover, only one type of tibia part is required for the different types of knee joint prostheses (at most different sizes, but no longer different types however), just because the movability is determined by the guiding element. Through this the cost and complexity in the manufacture is considerably reduced, since on the one hand different types of tibia parts need not be manufactured. Moreover, the technical manufacturing cost and complexity for projections, etc. for the securing of meniscus parts by means of snap connection or the like is also avoided. The same holds for the meniscus parts; thus no special meniscus parts need be manufactured for a knee joint prosthesis in which the meniscus part is to be immobile relative to the tibia part. The remaining disadvantages which have been arising up to now (lower thickness of the tibia plateau and/or partly extreme stressing in the peripheral regions of the meniscus part) also disappear.

At the same time however the intra-operative flexibility for the operating surgeon in regard to the type of the knee joint prosthesis to be implanted remains completely preserved. The surgeon can namely—in accordance with the actual anatomical conditions—still decide during the operation where necessary that a different type of knee joint prosthesis than the type which was planned prior to the operation represents the ideal care for the patient without it being necessary to provide additional prosthesis parts which are not contained in the kit.

In an advantageous exemplary embodiment of the kit in accordance with the invention the tibia part has a bore in its surface facing the femur part which is provided with a cut-out. The individual guiding elements have in each case a pin which protrudes into this bore in the tibia part when the prosthesis is assembled. In addition the guiding elements have in each case a guiding part which is in engagement with a corresponding guiding surface at the meniscus part when the prosthesis is assembled. Some of the pins have a projection which comes to lie in the cut-out of the bore, whereas other pins have no such projection.

Those guiding elements which have a pin with a projection are rotationally fixedly seated in the bore of the tibia part after the introduction of the pin there. This also holds for the guiding part belonging to the respective guiding element and thus also for the meniscus part which is in engagement with the guiding part. On the contrary those guiding elements which have no such projection are rotatably journalled, which also holds correspondingly for the guiding part and thus also for the meniscus part which is in engagement with the guiding part. The possibility of the translational displacement of the meniscus part along the guiding part will be discussed below.

In a further advantageous exemplary embodiment the meniscus part has an elongate hole in which the guiding part is received when the prosthesis is assembled. This exemplary embodiment is distinguished insofar as it can be particularly simply assembled during the operation. First, namely, the tibia part is usually secured to the prepared tibia and the femur part to the prepared femur. Then—depending on the prosthesis type—a corresponding guiding element can be inserted into the bore of the tibia part. Once this has taken place, then the meniscus part can be pushed over the guiding part of the guiding element and finally the knee joint repositioned.

It is particularly advantageous when guiding elements with different lengths of the guiding part are provided in the kit, so that for one and the same meniscus part, depending on the length of the guiding part, a translational movement of the meniscus part is either possible or is not possible when the prosthesis is assembled. This means that for a given meniscus part (e.g. with predetermined length of the elongate hole) it can be determined by the choice of the guiding element alone whether a translational displacement of the meniscus part along the guiding part should be permitted or not. This decision often depends on the state of the ligament apparatus. If such a translational displacement is to be permitted, then the length of the guiding part should be chosen to be shorter than the length of the elongate hole. If on the contrary no translational displacement of the meniscus part along the guiding part is to be permitted, then the length of the guiding part is to be chosen to be equal to the length of the elongate hole.

In a further advantageous exemplary embodiment of the kit in accordance with the invention the pin of the guiding element is formed as a hollow pin for the reception of a pin of a stabilizing element. This stabilizing element protrudes between the condyles of the femur part when the prosthesis is assembled and has means for the varus-valgus stabilizing. These means for the varus-valgus stabilizing can e.g. be stabilizing surfaces which cooperate with corresponding counter-surfaces. On the other hand the guiding element with the hollow pin can also be used alone, so that a guiding element which is formed in this manner does optionally allow the reception of a stabilizing element of this kind, but otherwise functions exactly as a guiding element in which the pin is formed as a full pin.

DETAILED DESCRIPTION OF SPECIFIC EXEMPLARY EMBODIMENTS

Figure 1:
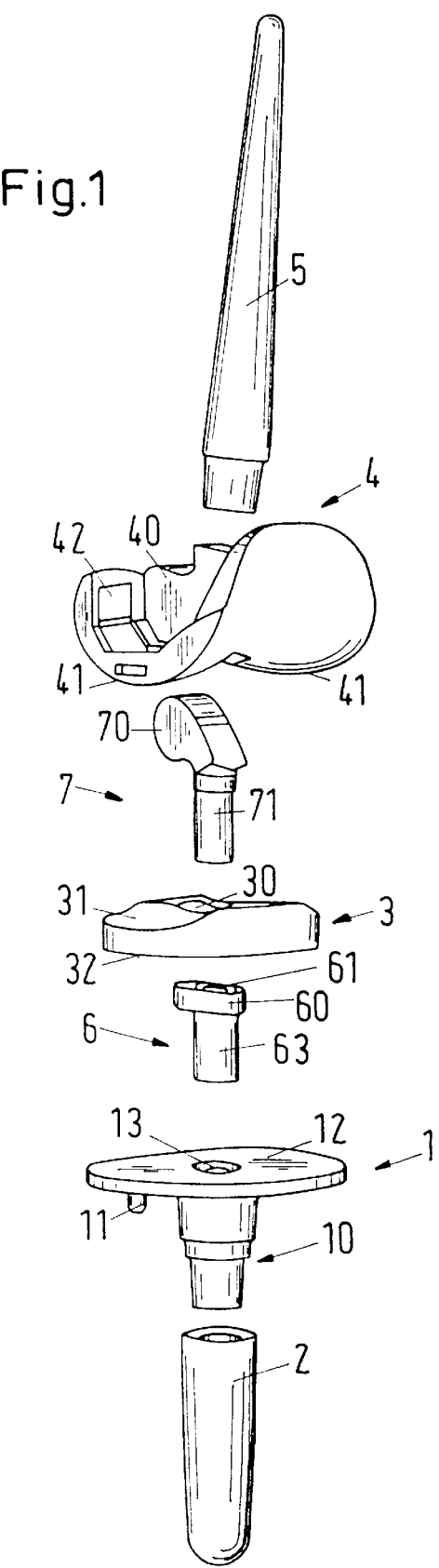
FIG. 1 illustrates an exemplary embodiment of a knee joint prosthesis which can be assembled with the help of the kit in accordance with the invention, in an exploded view.

In the exploded view shown in FIG. 1 of an exemplary embodiment of a special type of a knee joint prosthesis which can be assembled with a kit in accordance with the invention one recognizes a tibia part 1 which can be provided with an anchoring shaft 2 at its application piece 10 insofar as this is required by the condition of the tibia, which can be the case in particular in revision operations. At the lower side of the tibia part 1 e.g. two anchoring pins 11 are provided, of which only one can be recognized in FIG. 1. These anchoring pins 11 are introduced into correspondingly produced bores in the tibia and prevent a rotation of the tibia part 1 relative to the tibia. For reasons of draftsmanship the illustration of a cut-out for the rear cruciate ligament was dispensed with in the illustration of the tibia part 1; it can however be standardly provided in the tibia part 1 (see FIG. 2) so that the tibia part 1 can be universally used independently of the state of the ligaments.

Furthermore, one recognizes in FIG. 1 a femur part 4 which can be provided with an anchoring shaft 5 insofar as this is required by the condition of the femur, which can be the case in particular in revision operations. In this exemplary embodiment the femur part 4 has a stabilizing box 40 which is arranged between two condyles 41. Furthermore, one recognizes cement pockets 42 in which bone cement for the securing of the femur part 4 to the femur is located in a cemented implantation of the femur part 4.

Furthermore, a meniscus part 3 can be recognized in FIG. 1 which is arranged between the femur part 4 and the tibia part 1. The meniscus part 3 has an elongate hole 30 and two bearing shells 31, of which only one can be recognized in FIG. 1. The condyles 41 of the femur part 4 come to lie in the bearing shells 31 of the meniscus part 3 when the prosthesis is assembled.

The surface 12 of the tibia part 1 facing the femur part 4, often designated as the sliding surface in sliding menisci, is formed to be planar and is typically ground and/or polished. The lower side 32 of the meniscus part 3 is also designed to be planar and smooth, so that in principle both a translational and a rotational movement of the meniscus part 3 relative to the tibia part 1 are possible. The tibia part 1 also has a bore 13 in the surface 12 facing the femur part 4.

Furthermore, one recognizes in FIG. 1 a guiding element 6 having a pin 63 which protrudes into the bore 13 of the tibia part 1 when the prosthesis is assembled. Furthermore, the guiding element 6 has a guiding part 60 which is received in the elongate hole 30 of the meniscus part 3 when the prosthesis is assembled. Otherwise it can be recognized that the pin 63 of the guiding element is formed as a hollow pin; it has namely a bore 61 in which in this exemplary embodiment the pin 71 of a stabilizing element 7 is received when the prosthesis is assembled.

In this exemplary embodiment the stabilizing element 7 protrudes between the condyles 41 of the femur part 4 into the stabilizing box 40 when the prosthesis is assembled. There the stabilizing element 7 has two stabilizing surfaces 70 which together with the inner side walls of the stabilizing box 40 produce a varus-valgus stabilizing.

Figure 2:
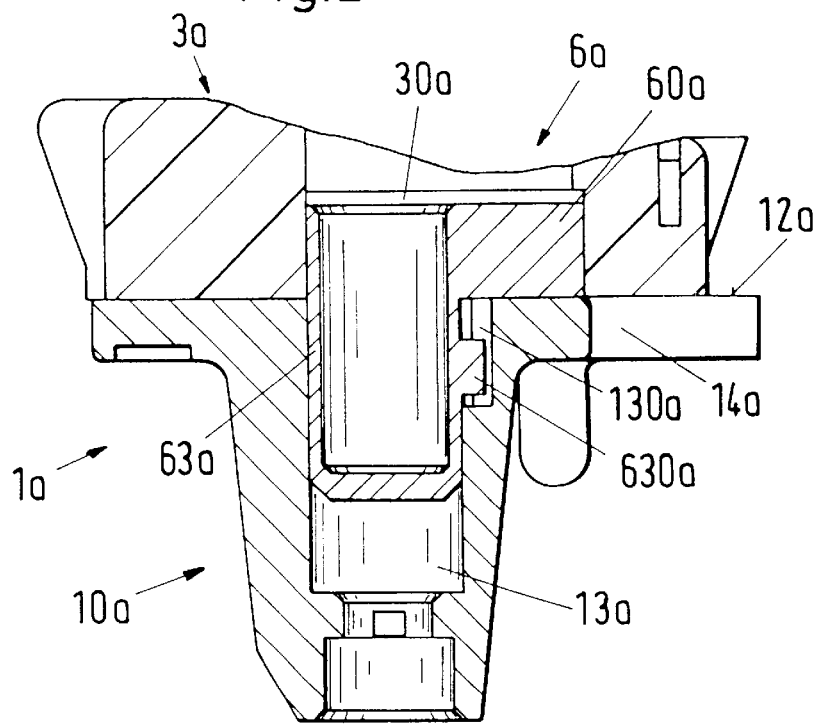
FIG. 2 illustrates an exemplary embodiment of a tibia part with the meniscus part placed on and with a guiding element which is arranged between the tibia part and the meniscus part and is in engagement with both of them.

FIG. 2 shows an exemplary embodiment of a tibia part 1a in which a cut-out 14a for the rear cruciate ligament is standardly provided. The tibia part 1a likewise has an application piece 10a in which an anchoring shaft (not illustrated in FIG. 2) can be received where appropriate. Furthermore, one recognizes the meniscus part 3a which is arranged on the surface 12a of the tibia part 1a facing the femur part (not illustrated).

Furthermore, one recognizes in FIG. 2 the guiding element 6a having a pin 63a which protrudes into the bore 13a of the tibia part 1a. The pin 63a of the guiding element 6a is formed here as a hollow pin. It has a bore 61a in which for example a stabilizing element (see FIG. 1) can be received. The actual reception of a stabilizing element is however merely optional; the guiding element 6a can be used equally well for other prosthesis parts without a stabilizing piece of this kind.

The guiding part 60a of the guiding element 6a is received in the elongate hole 30a of the meniscus part 3a, and indeed in such a manner that the guiding part is in engagement with at least one guiding surface at the meniscus part (here with the side walls of the elongate hole). In this exemplary embodiment the elongate hole 30a is formed to be graduated, so that the guiding element 30a can in no case slide out upwardly through the elongate hole 30a, but the meniscus part 3a can nevertheless be pushed from above over the guiding part 60a.

One recognizes in FIG. 2 that the length L of the guiding part 60a (see FIG. 3) and the length of the elongate hole 30a (at least in that part of the elongate hole in which the guiding part comes to lie) are equal. This has as a result that the meniscus part 3a cannot be displaced along the guiding part 60a. A translational displacement of the meniscus part 3a on the tibia part 1a along the guiding part 60a is thus excluded.

The pin 63a furthermore has a projection 630a which comes to lie in a cut-out 130a of the bore 13a in the tibia part 1a. The width b (FIG. 3) of this projection 63a is matched to the width of the cut-out 130a. During the introduction of the pin 63a the latter is introduced into the bore 13a of the tibia part 1a in such a manner that the projection 630a slides in into the cut-out 130a of the bore 13a at the pin 63a. Afterwards the pin 63a is rotationally fixedly seated relative to the tibia part 1a.

If now the meniscus part 3a with its elongate hole 30a is pushed from above over the guiding part 60a of the guiding element 6a, then the meniscus part 3a can also not be rotated relative to the tibia part 1a afterwards, since the width B (see FIG. 3) of the guiding element 6a is matched to the width of the elongate hole 30a. A translational displacement along the guiding part 60a is likewise eliminated since the length L of the guiding part 60a is matched to the length of the elongate hole 30a.

In the exemplary embodiment shown in FIG. 2 neither a translational nor a rotational movability of the meniscus part 3a relative to the tibia part 1a is possible. The meniscus part 3a is rather arranged so as to be immovable relative to the tibia part 1a.

Nevertheless, with the same tibia part 1a it is also possible to assemble other prosthesis types in which the meniscus part 3a is movable relative to the tibia part 1a in a different manner. For this one considers in the following the guiding element 6a in FIG. 3 or, respectively, an alternative guiding element 6b in FIG. 4, both of which are illustrated in a view from below. In this it will be assumed that at least the dimensions of the elongate hole of the meniscus part, if not of the entire meniscus part, remain unchanged.

Figure 3:
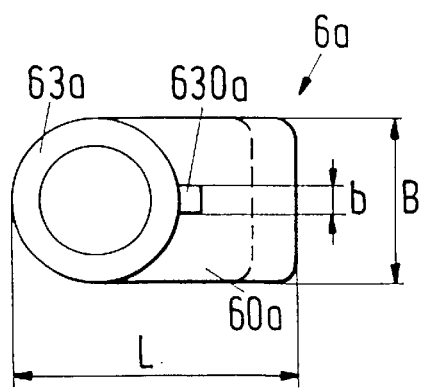
FIG. 3 is a view from below of the guiding element in accordance with FIG. 3.

If one first considers the guiding element 6a in FIG. 3, one recognizes that the guiding element 6a is rotationally fixedly seated relative to the tibia part 1a with the help of the projection 630a on the pin 63a, as has already been described above. If now a connecting rod is chosen with a shorter length L but with the same width B as previously, as is for example indicated in FIG. 3 by the broken line, then this means consequently that the meniscus part is admittedly translationally displaceable along the guiding part (in the anterior/posterior direction in FIG. 2) but is still not rotatable.

Figure 4:
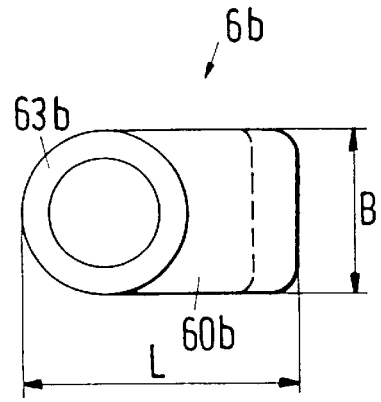
FIG. 4 is a view from below of an alternative guiding element.

If one wishes merely to achieve a rotatability of the meniscus part without a translational displaceability of the meniscus part on the tibia part, then one should choose the guiding element 6b in accordance with FIG. 4. This guiding element 4b is again matched with respect to its length L and width B to the length and width of the elongate hole, so that no translational displacement of the meniscus part relative to the tibia part is possible, although a rotation is possible. The pin 63b namely has no projection, so that the pin 63b is rotatably journalled in the bore of the tibia part. The rotatability of the pin 63b in the bore of the tibia part however has as a result that the guiding element 6b and thus ultimately also the meniscus part is rotatable relative to the tibia part.

Finally the case remains to be considered in which both a rotatability and a translational displaceability of the meniscus part relative to the tibia part are desired, which comes under consideration in particular when the ligament apparatus is intact. For this one should again choose the guiding element 6b in FIG. 4, however with a lesser length, as is indicated by the broken line in FIG. 4. The guiding element 6b is then rotatable relative to the tibia part, through which the meniscus part is also rotatable relative to the tibia part. Through the lesser length of the guiding part 60b with respect to the elongate hole of the meniscus part, the meniscus part is also translationally displaceable along the guiding part 60b.

As far as the translational displaceability is concerned, it is clear that in principle the meniscus part can also be replaced instead of the guiding element. The elongate hole of the meniscus part must then be chosen in its dimensions in such a manner that it is either matched to the length of the guiding part (no translational displacement possible) or that it is longer than the guiding part (translational displacement possible).

As far as the rotation is concerned, it is also possible to permit a limited rotatability through a variation of the width of the projection 630a (FIG. 3) of the pin 63a relative to the width of the cut-out 130a of the bore 13a if this is desired.

In summary it can be stated that practically all kinds in the spectrum of the movability of the meniscus part relative to the tibia part can be covered with one and the same tibia part. This spectrum of the movability extends from a meniscus part which is immobile relative to the tibia part up to a meniscus part which is both rotatable and translationally displaceable with respect to the tibia part. This can be achieved in this simple manner through the provision of a plurality of different guiding elements which are in engagement both with the tibia part and the meniscus part when the prosthesis is assembled. Alternatively,—as regards the translational displaceability—different meniscus parts can be provided which have an elongate hole of differing length.

Materials which are known per se come under consideration for the materials of the individual parts. As regards the tibia part, it can in principle be manufactured of a cobalt-chromium alloy. Insofar as a cement-less implantation is to take place, the parts which come into contact with the bone, in particular the lower side of the tibia part, the application piece, the anchoring pins, etc., can be coated with a porous titanium layer, which is particularly suitable for the growing in. The meniscus part is for example manufactured of polyethylene, in particular of ultra high molecular polyethylene, which has particularly good (namely practically no) wear properties. The guiding element can also be manufactured of a cobalt-chromium alloy, which likewise holds for the stabilizing element and also for the femur part. In cement-less implantations those parts of the femur part which come into contact with the bone can likewise be coated with a porous titanium layer.

What is claimed is:

1. A kit for a knee joint prosthesis, comprising a tibia part, a femur part and a meniscus part which is to be arranged between the femur part and the tibia part, said kit enabling the assembly of different prosthesis types in which the meniscus part is arranged to be immobile relative to the tibia part and of prostheses in which the meniscus part is arranged so as to be movable relative to the tibia part, wherein the kit comprises a plurality of guiding elements which are formed in such a manner that the respective guiding element is in engagement with the tibia part and with the meniscus part when the prosthesis is assembled and determines the movability of the meniscus part relative to the tibia part; wherein the tibia part has a bore in its surface facing the femur part which is provided with a cut-out and the individual guiding elements in each case have a pin which protrudes into this bore of the tibia part when the prosthesis is assembled; wherein the kit has a guiding part which is in engagement with a corresponding guiding surface at the meniscus part when the prosthesis is assembled; and wherein some of the pins have a projection which comes to lie in the cut-out of the bore, whereas other pins have no projections of this kind.

2. A kit in accordance with claim 1, wherein the meniscus part has an elongate hole in which the guiding part is received when the prosthesis is assembled.

3. A kit in accordance with claim 1, wherein guiding elements with different lengths of the guiding part are provided, so that for one and the same meniscus part, depending on the length of the guiding part, a translational movement of the meniscus part is either possible or not when the prosthesis is assembled.

4. A kit in accordance with claim 1, wherein the pin of the guiding element is formed as a hollow pin for receiving a pin of a stabilizing element which protrudes in between the condyles of the femur part when the prosthesis is assembled and has means for the varus-valgus stabilizing.

* * * * *